United States Patent
Sakurai et al.

(10) Patent No.: US 7,685,895 B2
(45) Date of Patent: Mar. 30, 2010

(54) SUBSTRATE INSPECTION DEVICE, SUBSTRATE INSPECTION METHOD, AND RECOVERY TOOL

(75) Inventors: Yoshio Sakurai, Tokyo (JP); Yutaka Ogawa, Tokyo (JP)

(73) Assignee: NAS Giken Inc., Tokyo (JP)

( * ) Notice: Subject to any disclaimer, the term of this patent is extended or adjusted under 35 U.S.C. 154(b) by 919 days.

(21) Appl. No.: 10/584,822

(22) PCT Filed: Jan. 27, 2005

(86) PCT No.: PCT/JP2005/001562
§ 371 (c)(1), (2), (4) Date: Jun. 26, 2006

(87) PCT Pub. No.: WO2005/073692
PCT Pub. Date: Aug. 11, 2005

(65) Prior Publication Data
US 2009/0151480 A1  Jun. 18, 2009

(30) Foreign Application Priority Data
Jan. 29, 2004 (JP) ............................. 2004-022267

(51) Int. Cl.
*G01M 19/00* (2006.01)
(52) U.S. Cl. ..................................... 73/865.8; 134/902
(58) Field of Classification Search ................ 73/865.8; 134/902
See application file for complete search history.

(56) References Cited

U.S. PATENT DOCUMENTS

| 4,564,280 | A | * | 1/1986 | Fukuda | ........................ 396/611 |
| 5,395,446 | A | * | 3/1995 | Kageyama et al. | ............ 118/52 |
| 5,527,707 | A | * | 6/1996 | Fukazawa | ..................... 436/72 |
| 5,633,172 | A | * | 5/1997 | Shimazaki | ................... 436/177 |

FOREIGN PATENT DOCUMENTS

| JP | 2-28533 | 1/1990 |
| JP | 2-229428 | 9/1990 |

(Continued)

OTHER PUBLICATIONS

Korean Office Action for Korean Application No. 10-2006-7012957, mailed on Nov. 17, 2008 (4 pages).

(Continued)

*Primary Examiner*—John Fitzgerald
(74) *Attorney, Agent, or Firm*—Osha•Liang LLP

(57) ABSTRACT

A substrate inspection device includes a substrate rotating device for holding a substrate on a holding surface and causing rotation, a disk having a disk body rotatably supported on a base and three lift cams fixed to an upper side of the disk body and formed with cam faces that are inclined surfaces inclined in the rotational direction, and a lifter having a lifter body with a support surface on which the substrate is mounted and guiding in the vertical direction and lifter driven sections respectively projecting to and fixed to a lower side of the lifter body, where lower sides of the lifter driven sections respectively contact the cam faces in a sliding manner at contact points, and if the contact points are moved to an upper side of the inclined surfaces the support surface becomes higher than the holding surface.

5 Claims, 11 Drawing Sheets

FOREIGN PATENT DOCUMENTS

| | | |
|---|---|---|
| JP | 2-272359 | 11/1990 |
| JP | 5-256749 | 10/1993 |
| JP | 5-283498 | 10/1993 |
| JP | 8-233709 | 9/1996 |
| JP | 11166882 A * | 6/1999 |
| JP | 2000186988 A * | 7/2000 |
| JP | 2000332072 A * | 11/2000 |
| JP | 2005236145 A * | 9/2005 |
| JP | 2006108364 A * | 4/2006 |
| KR | 2001-94965 A | 11/2001 |

OTHER PUBLICATIONS

International Search Report for PCT/JP2005/001562 dated May 10, 2005 (1 page).
Patent Abstracts of Japan 2-272359 dated Nov. 7, 1990 (2 pages).
Patent Abstracts of Japan 02-028533 dated Jan. 30, 1990 (2 pages).
Patent Abstracts of Japan 05-256749 dated Oct. 5, 1993 (14 pages).
Patent Abstracts of Japan 05-283498 dated Oct. 29, 1993 (12 [pages).
Patent Abstracts of Japan 08-233709 dated Sep. 13, 1996 (14 pages).
Patent Abstracts of Japan 02-229428 dated Sep. 12, 1990 (2 pages).

* cited by examiner

II - II CROSS SECTION

III - III CROSS SECTION

III - III CROSS SECTION

I-I CROSS SECTION

IV - IV CROSS SECTION

SUBSTRATE INSPECTION DEVICE, SUBSTRATE INSPECTION METHOD, AND RECOVERY TOOL

FIELD OF THE INVENTION

The present invention relates to a substrate inspection device and substrate inspection method for inspecting a substrate. In particular, the present invention relates to a substrate inspection device, substrate inspection method and recovery tool suitable for attaching a droplet to an outer surface of a substrate and moving the droplet along the outer surface in order to inspect the substrate.

BACKGROUND OF THE INVENTION

In a manufacturing facility or inspection facility for semiconductors and liquid crystals, a substrate inspection device is used.

A substrate inspection device is a device for inspecting a substrate. For example, a substrate may be a semiconductor wafer or a liquid crystal substrate. A semiconductor wafer is a wafer such as silicon, gallium, silicon carbide etc.

A substrate inspection device is required to position a substrate. Normally, in order to prevent contamination of a substrate, a simple and reliable positioning mechanism is required.

Also, some substrate inspection devices are used in order to accurately measure amounts of impurities, such as sodium, gallium, or iron, in a film such as an oxide film or nitride film formed on a surface of a semiconductor wafer. With these substrate inspection devices, accurate positioning of a substrate is important for accurate measurement of the impurity amount.

If impurities are contained within a thin film, such as an oxide film or nitride film formed on the surface of a semiconductor substrate, even if the amount of that impurity is microscopic, there will be a significant influence on the electrical characteristics of a semiconductor element.

There has, therefore, been a demand to suppress contamination of impurities from the wafer surface as much as possible in a semiconductor element manufacturing facility.

In order to do this, amounts of impurities existing on the surface of a semiconductor wafer must be accurately measured.

In recent years, amounts of impurities have been measured by holding the impurities in a fluoride solution, instead of using secondary ion mass spectrometry, Auger spectroscopic analysis, or neutron activation analysis to measure amount of impurities existing on a wafer surface. One example of a fluoride solution is HF (hydrogen fluoride) solution.

After dissolving an oxide film on the surface of a silicon wafer in an HF solution, the HF solution is collected, and analysis of impurities within the HF solution is carried out. If the amount of collected HF solution is small, impurity concentration becomes high, which improves measurement precision.

For example, after a substrate is exposed to vapor of HF solution and an oxide film of the substrate is dissolved, a droplet of HF solution on the surface of the substrate is distilled, and this droplet is moved while still attached to the surface of the substrate. Impurities within the oxide film are collected in the droplet. By measuring the amount of impurities inside the droplet, the amount of impurities on the substrate surface is examined.

Since the measurement precision is improved, a substrate inspection device that is capable of measuring amounts of impurities in only a designated region and performing accurate positioning is required. In particular, a substrate inspection device, substrate inspection method and recovery tool suitable for moving a droplet while still attached to a surface of a substrate, and collecting impurities in the droplet are required.

One or more embodiments of the present invention provide a substrate inspection device and substrate inspection method that can improve measurement precision, and a substrate inspection device, substrate inspection method, and recovery tool suitable for causing a droplet to adhere to an outer surface of a substrate and move along the outer surface.

SUMMARY OF THE INVENTION

In one aspect, the present invention relates to a substrate inspection device. In accordance with one or more embodiments of the present invention, a substrate inspection device for inspecting a substrate is provided with a substrate rotation device for holding a lower surface of a horizontal substrate from below on a holding surface and rotating about a rotational center axis oriented vertically, a base, being the fundamental structure, a disk having a disk body rotatably supported on the base in a horizontal direction with the rotational center axis as a center and three lift cams respectively fixed at three places on a circumference on an upper side of the disk body and forming cam faces formed by inclined surfaces that are inclined downward in one rotation direction with the rotational center axis as a center, and a lifter, having a lifter body with a support surface where a substrate can be mounted on an upper side and movably guided up and down on the base and restraining rotation, and three lifter driven sections that are members projecting downward toward and respectively fixed to three places on a circumference of the lifter body that has the rotational center axis as a center, wherein lower sides of the three lifter driven sections are respectively brought into contact with the three cam faces in a sliding manner at respective contact points, wherein if the contact points move to an upper side of the inclined surface the support surface becomes higher than the holding surface, while if the contact points move to a lower side of the inclined surface the support surface becomes lower than the holding surface.

With the above described structure of one or more embodiments of the present invention, a substrate rotating device holds a lower surface of a horizontal substrate from below on a holding surface and rotates about a rotational center axis oriented vertically, a base is the fundamental structure, a disk body of a disk is rotatably supported on the base in a horizontal direction with the rotational center axis as a center, the three lift cams of the disk are respectively fixed at three places on a circumference on an upper side of the disk and form cam faces formed by inclined surfaces that are inclined downward in one rotation direction with the rotational center axis as a center, a lifter body of the lifter has a support surface where a substrate can be mounted on an upper side and movably guided up and down on the base and restraining rotation, the three lifter driven sections are members projecting downward toward and respectively fixed to three places on a circumference of the lifter body that has the rotational center axis as a center, with lower sides of the three lifter driven sections respectively coming into sliding contacting with the three cam faces at respective contact points, so that if the contact points move to an upper side of the inclined surface the support surface becomes higher than the holding surface, while if the contact points move to a lower side of the inclined surface the support surface becomes lower than the holding surface, which means that if the disk is rotated in one rotational direction with respect to the base the contact points move to a lower side of the inclined surface and the support surface becomes lower than the holding surface, while if the disk is rotated in the other rotational direction with respect to the base the contact points move to an upper side of the inclined surface and the support surface becomes higher than the holding surface, the substrate can be moved between the support surface and the holding surface by a simple operation to rotate the disk, and frictional force at the contact points causes lifter play to be offset to one side enabling the base to be accurately positioned on the holding surface, and it is possible to improve the precision of inspection after that.

A few embodiments of the present invention will be described in the following. The present invention includes any of the embodiments described in the following, and also any combination of two or more of these disclosed embodiments.

Further, with the substrate inspection device in accordance with selected embodiments of the present invention, the cam faces are formed by an inclined surface and a horizontal surface connecting to the upper side end of the inclined surface and the contact points can move from the upper side of the inclined surface to the horizontal surface.

With the above described structure of the invention, because the contact points can move from the upper side of the inclined surface to the horizontal surface, in a state where the horizontal surface is higher than the holding surface, when the substrate is mounted on the support surface or removed from the support surface, the lifter is stopped in a stable manner.

Further, with a substrate inspection device of an embodiment of the present invention, the base has a base plate member that is a plate-shaped member made level at an upper surface, a base cylinder member that is a cylindrical member having a central axis oriented vertically, and a base positioning mechanism that can align a central axis of the base cylinder member with the rotational center axis, while the disk body has a disk plate member, being a plate member, movably supported at three places on a circumference centered on the rotational center axis of a lower side in a horizontal direction on an upper surface of the base plate member, and three circumferential guides, fixed to the disk plate member and being members respectively brought into sliding contact with three places on the circumference of an outer surface of the base cylinder member.

In this embodiment of the present invention, because the base plate member of the base is a plate-shaped member made level at an upper surface, the base cylinder member of the base has a vertical central axis, the base positioning mechanism of the base aligns a central axis of the base cylinder member and the rotational center axis, the disk plate member of the disk body is a plate member movably supporting three places on a circumference centered on the rotational center axis of a lower side in a horizontal direction on an upper surface of the base plate member, and the three circumferential guides of the disk body are fixed to the disk plate member and respectively brought into sliding contact with three places on the circumference of an outer surface of the base cylinder member, the disk is rotated with high precision with the rotational center axis as a center, frictional force at the contact points causes the lifter to rotate with the rotational center axis as a center enabling the lifter play to be offset to one side, it is possible to position the substrate on the holding surface with good precision, and it is possible to improve precision of inspection after that.

Still further, with a substrate inspection device of an embodiment of the present invention, the substrate rotating device has a substrate holding member for holding a lower surface of a leveled substrate from below at a the holding surface, and a substrate holding base for rotatably supporting the substrate holding member turning around the rotational center axis, while the base positioning mechanism has a set screw for adjusting the size of a clearance between a side surface of the substrate holding base and an inner surface of the base cylinder member.

In one embodiment of the present invention, because the substrate holding member of the substrate rotating device holds a lower surface of a leveled substrate from below at a the holding surface, the substrate holding base of the substrate rotating device rotatably supports the substrate holding member turning around the rotational center axis, and the set screw of the base positioning mechanism adjusts the dimension of a clearance between a side surface of the substrate holding base and an inner surface of the base cylinder member, it is possible to adjust the position of the lifter supported on the base easily and with good precision with the rotational center axis as a reference.

Yet further, with a substrate inspection device of an embodiment of the present invention, the lifter body has a lifter plate member with a support surface on which a substrate can be mounted on an upper side, being a plate member, and three wafer holders respectively arranged and fixed at three places on a circumference of the support surface of the lifter plate member with the rotational center axis as a center, and an edge of a substrate placed on the support surface contacts the three wafer holders from the circumference.

In such an embodiment, because the lifter plate member of the lifter body has a support surface on which a substrate can be mounted on an upper side, being a plate member, the three wafer holders of the lifter body are respectively arranged and fixed at three places on a circumference of the support surface of the lifter plate member with the rotational center axis as a center, and an edge of a substrate placed on the support surface contacts the three wafer holders from the circumference, the substrate is positioned on the support surface with good precision and it is possible to improve positional precision of the substrate when mounting the substrate on the support surface.

Further, with a substrate inspection device of an embodiment of the present invention, the base has a base plate member that is a plate-shaped member made level at an upper surface, and three base vertical guides that are cylindrical members having a vertical central axis, and respectively fixed at three locations on a circumference on an upper side of the base plate member with the rotational center axis as a center, while the lifter body has a lifter plate member with a support surface on which a substrate can be mounted on an upper side, being a plate member, and three lifter vertical guides, being cylindrical members with vertical central axes, respectively fixed at three places of the lifter plate member, either the base vertical guides or the lifter vertical guides have hollow sections, while the others fit into the hollow sections, with the lifter being guided so as to move vertically on the base with restricted rotation.

In such an embodiment of the present invention, because the base plate member of the base is a plate member made level at an upper surface, the three base vertical guides of the base are respectively fixed at three places on a circumference on an upper side of the base plate member with the rotational center axis as a center and have a vertical central axis, the lifter plate member of the lifter body has a support surface on which a substrate can be mounted on an upper side, being a plate member, the three lifter vertical guides of the lifter body are cylindrical members with vertical central axes respectively fixed at three places of the lifter plate member, one of the base vertical guide and the lifter vertical guides has a hollow space, the other is fitted into the hollow space, and the lifter is movably guided in the vertical direction on the base with rotation restricted, if frictional force of the contact points causes the lifter to rotate about the rotational center axis play in the hollow space of the base vertical guide and the lifter vertical guides is offset to one side, it is possible to position the substrate on the holding surface with good accuracy and it is possible to improve precision of inspection after that.

Also, a substrate inspection device in accordance with an embodiment of the present invention for adhering a droplet to a substrate and causing movement in order to inspect the substrate comprises a substrate rotating device for holding a horizontal substrate and rotating the substrate about a rotational center axis oriented vertically, a recovery tool having a cylindrical section with a central axis oriented vertically, having an internal space capable of accumulating the droplet, and a drive unit capable of moving the recovery tool in the horizontal direction, wherein the cylindrical section is provided at a side section with a groove extending horizontally to connect the internal space to atmospheric space, and when a droplet is accumulated in the internal space and the substrate is rotated, the drive unit is capable of holding the recovery tool so that a droplet exposed to the groove comes into contact with an edge of the substrate.

In an embodiment of the invention, because the substrate rotating device holds a horizontal substrate and causes rotation about a rotational center axis oriented vertically, the recovery tool has a cylindrical section with a central axis oriented vertically, having an internal space capable of accumulating a droplet, and the drive unit is capable of moving the recovery tool in the horizontal direction, with the cylindrical section being provided with a groove extending horizontally to connect the internal space to atmospheric space, and when a droplet is accumulated in the internal space and the substrate is rotated, the drive unit being capable of holding the recovery tool so that a droplet exposed to the groove comes into contact with an edge of the substrate, it is possible to cause a droplet to adhere to the edge of the substrate and the droplet moves along the edge.

Also, a substrate inspection device in accordance with an embodiment of the present invention for adhering a droplet to a substrate and causing movement in order to inspect the substrate comprises a substrate rotating device for holding a horizontal substrate and rotating about a rotational center axis oriented vertically, a recovery tool having a cylindrical section with a central axis oriented vertically, having an internal space capable of accumulating a droplet, a drive mechanism capable of moving the recovery tool in the horizontal direction, and negative pressure maintaining means capable of maintaining pressure of the internal space at a pressure more negative than atmospheric pressure when liquid has been collected in the internal space, wherein the cylindrical section is provided with a first through hole connecting the internal space to atmospheric space at a lower end, and when a droplet is accumulated in the internal space and the substrate is rotated, the drive mechanism is capable of holding the recovery tool so that a distance between the surface of the substrate and the lower end of the cylindrical section is kept constant.

In an embodiment of the present invention, because the substrate rotating device holds a horizontal substrate and causes rotation about a rotational center axis oriented vertically, the recovery tool has a cylindrical section with a central axis oriented vertically, having an internal space capable of accumulating a droplet, the drive mechanism is capable of moving the recovery tool in the horizontal direction, the negative pressure maintaining means is capable of maintaining pressure of the internal space at a pressure more negative than atmospheric pressure when liquid has been collected in the internal space, the cylindrical section is provided with a first through hole connecting the internal space to atmospheric space at a lower end, and, when a droplet is accumulated in the internal space and the substrate is rotated, the drive mechanism is capable of holding the recovery tool so that a distance between the surface of the substrate and the lower end of the cylindrical section is kept constant, a pulling force due to the negative pressure acts on the droplet accumulated in the internal space, and it is possible to prevent a droplet flowing out to a lower side from the first through hole of the recovery tool.

An embodiment of the present invention will be described in detail in the following. The present invention includes any of the embodiments described in the following, and also any combination of two or more of these disclosed embodiments.

Further, with a substrate inspection device of an embodiment of the present invention, the circumference of an edge of the first through hole at the lower end of the cylindrical section forms an annular level surface.

In one embodiment of the present invention, because the circumference of an edge of the first through hole at the lower end of the cylindrical section forms an annular level surface, a droplet coming out downward from the first through hole is pulled by adhesion of the level surface, and it is possible to control leaking out of the droplet to a lower side from the first through hole of the recovery tool.

Still further, with a substrate inspection device of an embodiment of the invention, the cylindrical section is respectively provided at side sections with a plurality of second through holes having central axes that cross in the same direction with respect to the radial direction, and the second through holes connect the internal space and the atmospheric space.

In one embodiment of the present invention, the plurality of second through holes that are provided in a side section of the cylindrical section have axial centers that cross in the same direction with respect to the radial direction, and connect the internal space and the atmospheric space, which means that vapor passes from an outer side space of a side section through the second through holes and enters the internal space, a droplet accumulated in the internal space is swirled about and pulled upward to the negative pressure.

Further, with a substrate inspection device of an embodiment of the present invention, the negative pressure maintaining means has a negative pressure pipe connecting to the internal space.

With the above-described structure of the present invention, because the negative pressure maintaining means has a negative pressure pipe connecting to the internal space, vapor inside the internal space is pulled upward.

Also, a recovery tool in accordance with embodiments of the present invention for adhering a droplet to the substrate and causing movement in order to inspect the substrate, comprises a cylindrical section with a central axis oriented vertically, having an internal space capable of accumulating a droplet, wherein the cylindrical section is provided at a side section with a groove extending horizontally to connect the internal space to an atmospheric space.

In one embodiment of the invention, because the recovery tool comprises a cylindrical section, with axial centers facing vertically having an internal space capable of accumulating a droplet, and the cylindrical section is provided with a groove extending horizontally to connect the internal space to atmospheric space in a side section, if a droplet is accumulated in the internal space and the recovery tool is held so that a droplet exposed to the groove is brought into contact with the edge of the substrate and moved along the edge, it is possible to adhere the droplet to the edge of the substrate and move the droplet along the edge.

Also, in one embodiment, a recovery tool of the present invention for adhering a droplet to the substrate and causing movement in order to inspect the substrate is provided with a cylindrical section with a central axis oriented vertically, having an internal space capable of accumulating a droplet, and negative pressure maintaining means capable of maintaining pressure of an internal space at a more negative pressure than the atmospheric pressure when a droplet has been accumulated in the internal space, the cylindrical section being provided with a first through hole connecting the internal space with atmospheric space at a lower end.

In one embodiment, the recovery tool has a cylindrical section with a central axis oriented vertically, having an internal space capable of accumulating a droplet, and the negative pressure maintaining means can maintain pressure of the internal space at a pressure more negative than atmospheric pressure when liquid has been collected in the internal space, and the cylindrical section is provided with a first through hole connecting the internal space to atmospheric space at a lower end, if a droplet has been accumulated in the internal space and the recovery tool is held so that a distance between the surface of the substrate and the lower end of the cylindrical section is kept constant, and movement is caused along the surface of the substrate, an upward pulling force due to the negative pressure acts on the droplet accumulated in the internal space, and it is possible to control a droplet flowing out to a lower side from the first through hole of the recovery tool.

A few embodiments of the present invention will be described in detail in the following. The present invention includes any of the embodiments described in the following, and also any combination of two or more of these disclosed embodiments.

Further, with a recovery tool of an embodiment of the present invention, the circumference of an edge of the first through hole at the lower end of the cylindrical section forms an annular level surface.

In one embodiment, because the circumference of an edge of the first through hole at the lower end of the cylindrical section forms an annular level surface, a droplet coming out downward from the first through hole is pulled by adhesion of the level surface, and it is possible to control leaking out of the droplet to a lower side from the first through hole of the recovery tool.

Still further, with a recovery tool of an embodiment of the invention, the cylindrical section is respectively provided at side sections with a plurality of second through holes having central axes that cross in the same direction with respect to the radial direction, and the second through holes connect the internal space and the atmospheric space.

In one embodiment, the plurality of second through holes that are provided in a side section of the cylindrical section have central axes that cross in the same direction with respect to the radial direction, and connect the internal space and the atmospheric space of the side section, which means that vapor passes from an outer space of the side section through the second through holes and enters the internal space, a droplet accumulates in the internal space are swirled about and pulled upward to the negative pressure.

Further, with a recovery tool of an embodiment of the present invention, the negative pressure maintaining means has a negative pressure pipe connecting to the internal space.

In one embodiment, because the negative pressure maintaining means has a negative pressure pipe connecting to the internal space, vapor inside the internal space is pulled upward.

Also, in one embodiment, a substrate inspection method of the present invention for adhering a droplet to the substrate and causing movement in order to inspect the substrate comprises a substrate inspection device preparation step for preparing the above disclosed substrate inspection device, a substrate setting step for setting the substrate in the substrate rotating device, a solution dropping step for dropping a solution in to the internal space, a negative pressure maintaining step where the negative pressure maintaining means maintains pressure in an internal space at a more negative pressure than the atmospheric pressure, and a substrate scanning step where the drive unit keeps a distance between the surface of the substrate and a lower end of the cylindrical section constant when the substrate is rotated.

In one embodiment, because the above disclosed substrate inspection device is prepared in a substrate inspection device preparation step, a substrate is set in the substrate rotating device in a substrate setting step, a solution is dropped in to the internal space of the recovery tool in a solution dropping step, the negative pressure maintaining means maintains pressure in an internal space at a more negative pressure than the atmospheric pressure in a negative pressure maintaining step, and the drive mechanism keeps a distance between the surface of the substrate and a lower end of the cylindrical section constant when the substrate is rotated in a substrate scanning step, it is possible to control leakage of a droplet that has accumulated in the internal space to the surface of the substrate, moving the surface of the substrate, a droplet is still attached to the surface of the substrate.

Further, with a substrate inspection method of an embodiment of the present invention, the substrate setting step involves setting a substrate having a surface with hydrophilic properties with respect to the solution in the substrate rotating device.

In one embodiment, it is possible to control leakage of a droplet that has accumulated in the internal space to the surface of the substrate even if the surface of the substrate has hydrophilic properties with respect to the solution, while being able to move the surface of the substrate with the droplet attached to the substrate surface.

In one or more embodiment, a substrate inspection device relating to the invention as described above, because of the method and structure, may provide the following features.

Rotation of a lifter having a support surface for mounting a substrate is restricted, lift cams are arranged on a disk so that inclination of inclined surfaces face in a circumferential direction for rotation about a rotational central axis of the substrate, and if the contact points between the lifter and the inclined surfaces are caused to move along the inclined surface, then a substrate is mounted on the holding surface, when inspecting the substrate, the support surface is moved between an upper side and a lower side of the height of the holding surface, which means that if the disk is rotated on one rotation direction in the circumferential direction with respect to the base, the contact points move to the lower side of the inclined surfaces and the support surface becomes lower than the holding surface, while if the disk is rotated in the other rotational direction in the circumferential direction with respect to the base, the contact points move to an upper side of the inclined surfaces and the support surface becomes higher than the holding surface, and it is possible to switch the substrate between the support surface and the holding surface with the simple operation of rotating the disk, frictional force at the contact points causes play of the lifter to be offset to one side enabling accurate positioning of the substrate, and it is possible to improve inspection precision after that.

Also because the contact points move from the upper side of the inclined surfaces to a horizontal surface, in a state where the horizontal surface is higher than the holding surface, when mounting the substrate on the support surface, or taking the substrate off the support surface, the lifter is stopped in a stable manner.

Further, since a plate-shaped member and a cylindrical member are provided on the base, and the disk is move rotationally contacting the plate-shaped member and the cylindrical member at three places respectively, the disk is accurately rotated with the rotational center axis as a center, frictional force at the contact points causes the lifter to be rotated about the rotational center axis and play of the lifter can be offset to one side, it is possible to accurately position the substrate on the holding surface, and it is possible to improve inspection precision after that.

Since a horizontal position of the base is adjusted by set screws pushing a base of the disk rotating device, the position of the lifter supported on the base can be accurately adjusted easily with the rotational center axis as a reference.

Since the edge of the substrate mounted on the support surface of the lifter is contacted by three members, it is possible to improve accuracy of substrate position when mounted on the holding surface.

Also, vertical guides are provided for respectively guiding the base and the lifter moving vertically, one of the base vertical guides and one of the lifter vertical guides has a hollow section, another is fitted into the hollow section, the lifter is guided to move vertically on the base, and rotation of the lifter is restricted.

A leveled substrate is rotated, and a groove is provided extending horizontally in a side surface of the recovery tool having an internal space capable of accumulating a droplet, and the drive mechanism is capable of holding the recovery tool so that the droplet exposed to the groove is brought into contact with the edge of the substrate, which means that it is possible to cause the droplet to adhere to the edge of the substrate and move along the edge Further, the leveled substrate is rotated, a through hole is provided in a lower end of the recovery tool having an internal space capable of accumulating a droplet, and the internal space can be made negative pressure, which means that an upward pulling force due to the negative pressure is made to act on the droplet accumulated in the internal space, and it is possible to control leakage of the droplet downward from the first through hole of the recovery tool.

Since the periphery of the edge of the first through hole in the lower end of the cylindrical member is made an annular flat surface, a droplet that drops down from the first through hole is pulled by the adhesive force of the horizontal surface, and it is possible to prevent leakage of the droplet to the lower side from the first through hole of the recovery tool.

Also, second through holes are respectively provided in side sections of the cylindrical member, facing in the same direction crossing the radial direction, and connecting the internal space and an outer space of the side section, which means that vapor passes from the outer space in the side section through the second through holes and enters the internal space, the droplet accumulated in the internal space is swirled about, and pulled upward in a twisting manner by the negative pressure.

Negative pressure piping of the negative pressure maintaining means connects to an upper section sealing off the internal space, and so vapor of the internal space is pulled upward.

Adopting a substrate inspection device provided with a recovery tool having negative pressure maintaining means, with the pressure of the internal space being kept at negative pressure a droplet of the recovery tool is made to adhere to the surface of the substrate and the surface of the substrate is moved, which means that it is possible to control leakage of the droplet that has accumulated in the internal space to the surface of the substrate while moving the substrate surface with the droplet still adhered to the surface of the substrate.

It is possible to control leakage of a droplet that has accumulated in the internal space to the surface of the substrate even if the surface of the substrate has hydrophilic properties with respect to the droplet, while being able to move the surface of the substrate with the droplet attached to the substrate surface.

Accordingly, it is possible to provide a substrate inspection device that can further improve measurement precision, and a substrate inspection device, substrate inspection method and a recovery tool suitable for measuring impurities existing in a substrate.

DETAILED DESCRIPTION

The following is a description, with reference to drawings, of an embodiment of implementing the present invention.

Figure 1:
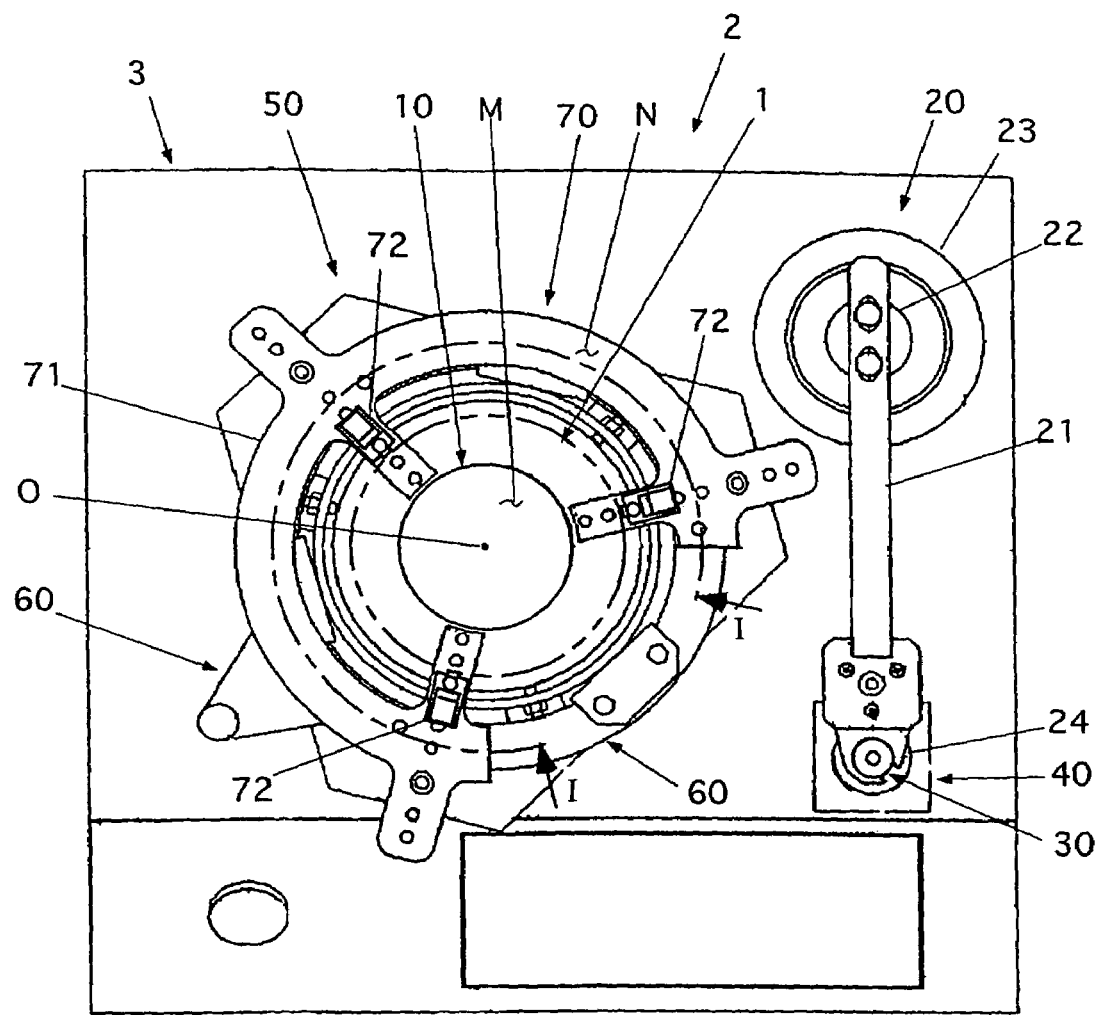
FIG. 1 is a plan view of a substrate inspection device of an embodiment of the present invention.
Figure 2:
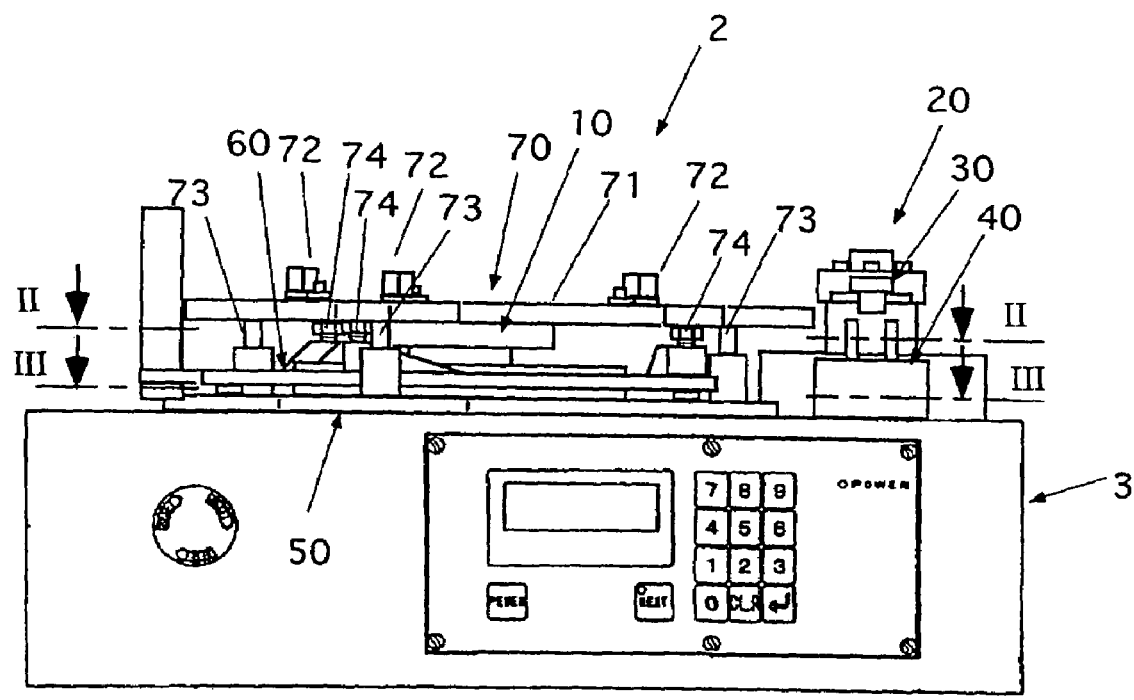
FIG. 2 is a front view of a substrate inspection device of an embodiment of the present invention.
Figure 3:
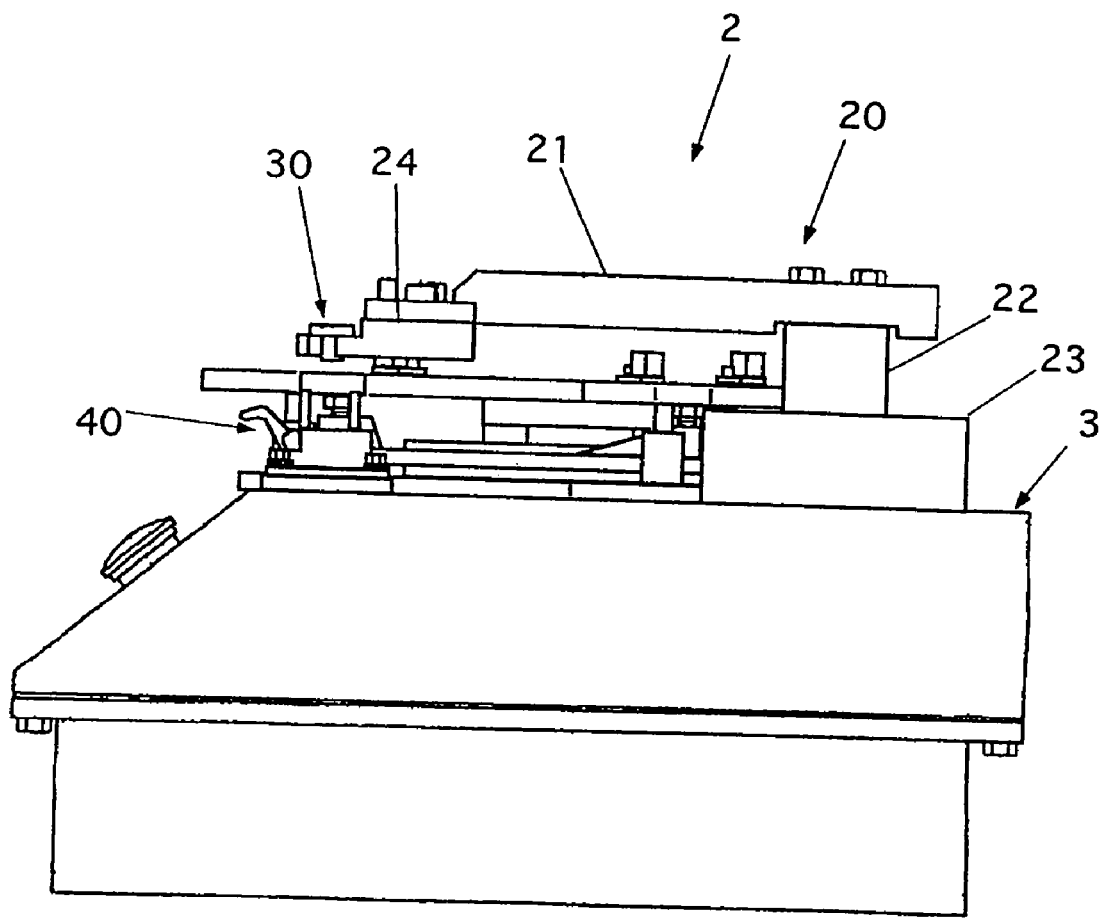
FIG. 3 is a side view of a substrate inspection device of an embodiment of the present invention.

FIG. 1 is a plan view of a substrate inspection device of an embodiment of the present invention. FIG. 2 is a front view of a substrate inspection device of an embodiment of the present invention. FIG. 3 is a side view of a substrate inspection device of an embodiment of the present invention.

A substrate inspection device 2 is a device for inspecting a substrate 1.

In the following, substrate inspection device 2 will be described with an example for the case where an amount of impurities existing in the substrate 1 is inspected.

In the case where a substrate is a silicon wafer, in inspecting the amount of impurities existing in the substrate 1, with a first method a surface of a substrate is bleached in liquid vapor (for example, vapor of an aqueous solution of HF (hydrogen fluoride)), to dissolve an oxide film on the surface of the substrate 1 in the fluid. After that, a droplet is adhered to the substrate 1 and moved in order to inspect the substrate 1, using the substrate inspection device. With a second method, liquid (for example vapor of an aqueous solution of HF (Hydrogen fluoride)) is dripped onto the surface of the substrate. An oxide layer of the surface of the substrate 1 is dissolved by the liquid. After that, a droplet is adhered to the substrate 1 and moved in order to inspect the substrate 1, using the substrate inspection device.

With the substrate inspection device, a droplet (for example HF solution) is dripped onto the surface of the substrate 1, the droplet is moved so as to run over a specified region of the surface of the substrate, and the droplet is recovered. The amount of impurities mixed in with the droplet is measured, and so it is possible to specify the impurity amount existing in a specified region of the surface of the substrate.

The substrate inspection device comprises a lower structure 3, a substrate rotating device 10, a drive unit 20, a recovery tool 30, a recovery tool setting unit 40, a base 50, a disk 60, and a lifter 70.

The lower structure 3 is a structure whose upper surface is mounted by the substrate rotating device 10, drive unit 20, recovery tool 30, recovery tool setting unit 40, base 50, disk 60, and lifter 70, and includes a controller and control face for controlling these components.

The substrate rotating device 10 is a unit for holding a lower surface of a leveled substrate from below on a holding surface M and rotating about a vertical rotational center axis, and is made up of a substrate holding member 11 and a substrate holding base 12.

The substrate holding member 11 is a member for holding a lower surface of a leveled substrate 1 from below at a holding surface M. A vacuum chuck mechanism is provided on the holding surface M. The vacuum chuck mechanism fixes the substrate 1, held on the holding surface M, using negative pressure.

The substrate holding base 12 is a unit for supporting the substrate holding member 11 so as to rotate about a rotational center axis.

The recovery tool 30 is a tool having an internal space H capable of accumulating a droplet.

Three types of recovery tool 30 having different structures will be described in the following based on the drawings. The recovery tools will be referred to respectively as first to third type recovery tools 30a, 30b, and 30c.

Initially the structure of a first type recovery tool of an embodiment of the present invention will be described.

Figure 8A:
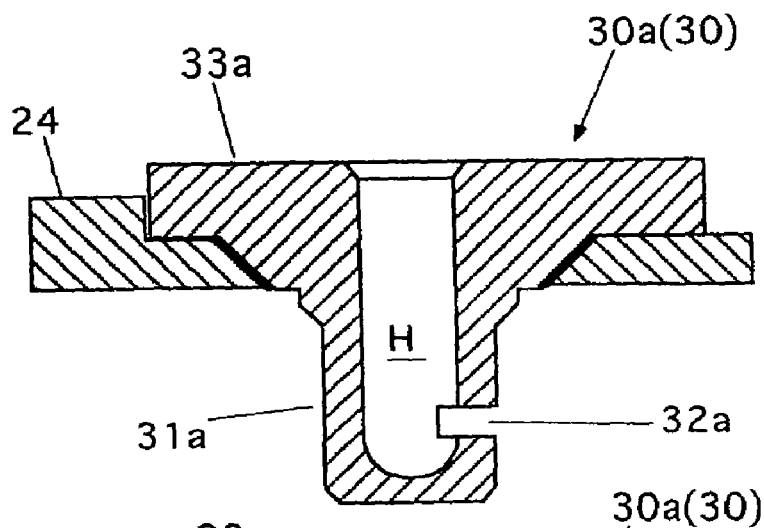
FIG. 8A is a cross section of a recovery tool of an embodiment of the present invention.
Figure 8B:
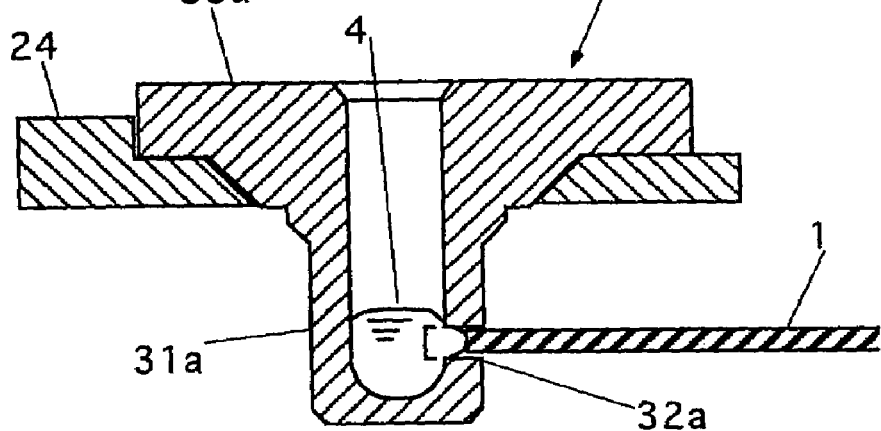
FIG. 8B is a cross section of a recovery tool of an embodiment of the present invention.
Figure 8C:
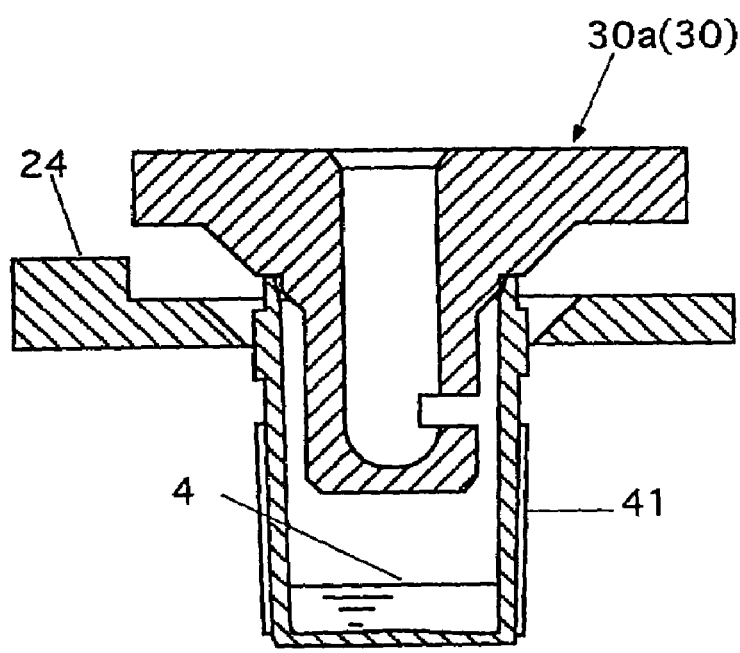
FIG. 8C is a cross section of a recovery tool of an embodiment of the present invention.

FIG. 8A to FIG. 8C are cross sections of a first type recovery tool of an embodiment of the present invention.

The first type recovery tool 30a is a tool that causes a droplet to come into contact with an edge of a substrate, and comprises a cylindrical section 31a and a flange section 33a.

The cylindrical section 31a has an internal space H capable of accumulating a droplet, and has a central axis oriented vertically. The cylindrical section 31a is provided at a side section with a groove 32a being larger in width than the thickness of the substrate, extending horizontally, and connecting the internal space H with an atmospheric space. The lower end of the cylindrical section 31a is closed.

A drive mechanism, that will be described later, is capable of holding the recovery tool 30a so that a droplet exposed to the groove 32a is brought into contact with the edge of the substrate.

The flange section 33a is an upper structure of the recovery tool 30a. A lower surface of the flange section 33a is formed in a tapered shape projecting downward. The tapered shape engages with a downwardly indented tapered section of the recovery tool holder 24, which will be described later. A groove section engaging with an opening of a container 41 is formed at a lower side of the tapered shape.

If a droplet accumulates in the internal space H, a part of the droplet is exposed to the groove 32a. By appropriately selecting the size and position of the groove 32a, it is possible to prevent a droplet leaking out from the groove 32a. This is considered to be because surface tension arising in the droplet and pressure such that there would be leakage from the groove 32a are equal.

Next, the structure of a second type recovery tool of an embodiment of the present invention will be described.

FIG. 9A to FIG. 9C and FIG. 10 are cross sections of a second type recovery tool of an embodiment of the present invention.

The second type recovery tool 30b is a tool that causes a droplet to come into contact with a surface of a substrate, and comprises a cylindrical section 31b, a flange section 34b, and negative pressure maintaining means 35b.

The recovery tool 30b is suitable for bringing a droplet into contact with a substrate surface that is hydrophilic. For example, in the case where the droplet is a solution of HF and an oxide film is formed on the surface of the substrate, if the recovery tool 30b is used, notable effects are achieved.

The cylindrical section 31b has an internal space H capable of accumulating a droplet, and has a central axis oriented vertically. The cylindrical section 31b has a first through hole 32b connecting the internal space H with an atmospheric space provided at a lower end. The periphery of the edge of the first through hole 32b in the lower end of the cylindrical section 31b is preferably an annular flat surface.

In particular, it is preferable for a plurality of second through holes 33b to be provided in a side section of the cylindrical section 31b, having axial centers that cross in the same direction with respect to the radial direction, and connecting the internal space H and an outer side space of the side section.

The drive unit, which will be described later, can hold the recovery tool when the substrate is rotated so that a distance between the surface of the substrate 1 and the lower end of the cylindrical section 31b is held constant.

By doing this, negative pressure draws the droplet that has accumulated in the internal space H upward, and adhesive force between the droplet and the recovery tool can cause a droplet caught in the gap between the surface of the substrate 1 and the lower end of the cylindrical section 31b to be attached to a leveled lower end of the cylindrical section 31b. As a result, it is possible to control a droplet leaking out to the surface of the substrate even if the droplet is hydrophilic with respect to the material of the surface of the substrate. For example, in the case where there is an oxide film on the surface of the substrate and the droplet is a solution (for example, HF solution) for dissolving the oxide film, the droplet of the HF solution is hydrophilic with respect to the oxide film, but there is no leakage of the HF solution from the internal space H. If a specified time elapses, the oxide film is dissolved and the base material of the substrate is exposed. Since the HF solution is hydrophobic with respect to the base material of the substrate, it flies away from the surface of the substrate due to surface tension.

Next, the structure of a third type recovery tool of an embodiment of the present invention will be described.

Figure 11A:
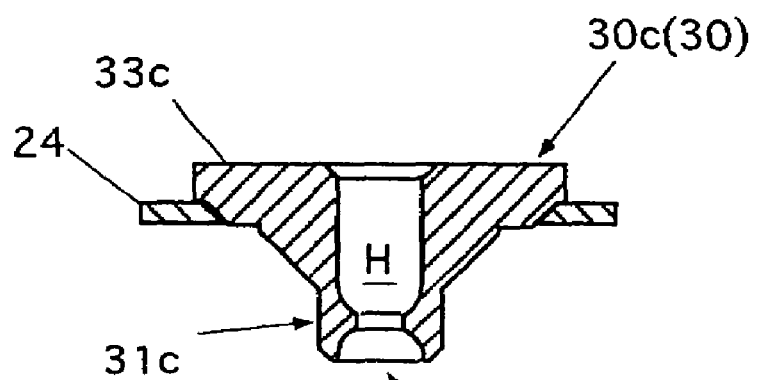
FIG. 11A is a cross section of a recovery tool of an embodiment of the present invention.
Figure 11B:
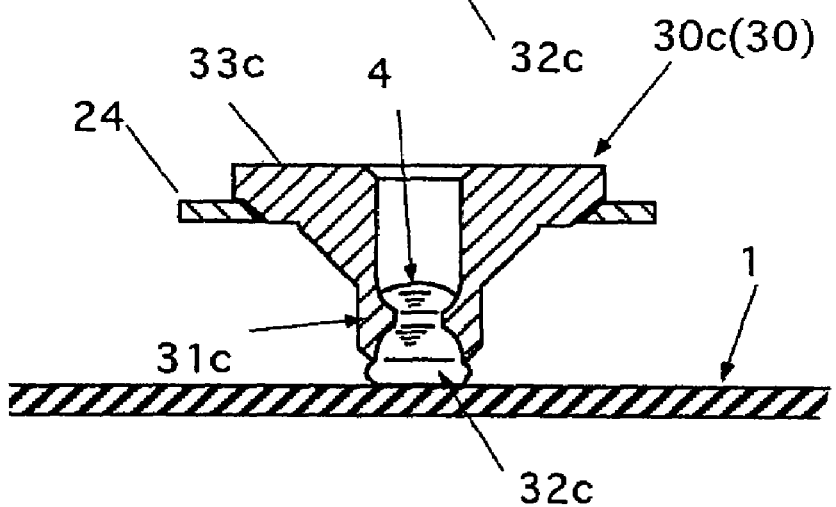
FIG. 11B is a cross section of a recovery tool of an embodiment of the present invention.
Figure 11C:
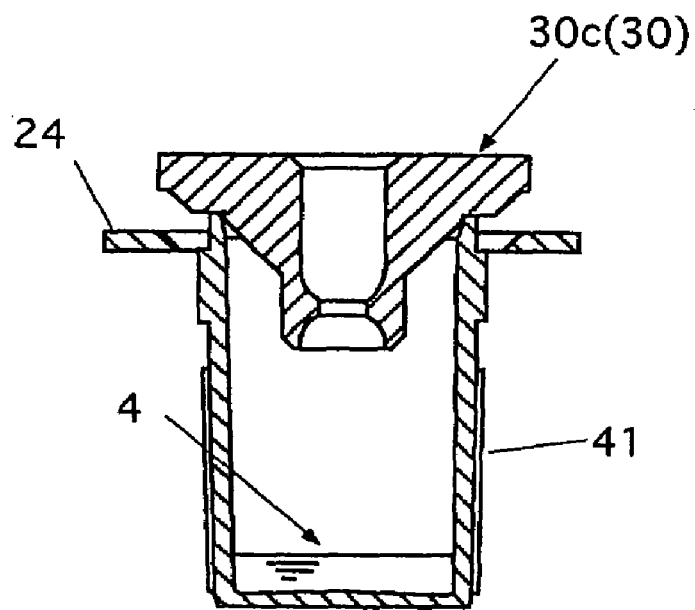
FIG. 11C is a cross section of a recovery tool of an embodiment of the present invention.

FIG. 11A to FIG. 11C are cross sections of a third type recovery tool of an embodiment of the present invention.

The third type of recovery tool 30c is a tool that causes a droplet to come into contact with a surface of a substrate, and comprises a cylindrical section 31c and a flange section 33c.

The cylindrical section 31c has an internal space H at the center of the inside, with an axial center oriented vertically and a first through hole 32C provided in a lower end of the cylindrical section 31c. The first through hole 32c connects the internal space H with an atmospheric space. The periphery of the edge of the first through hole in the lower end of the cylindrical section is preferably an upwardly concave hollow.

The drive unit, which will be described later, can keep a distance between the surface of the substrate 1 and the lower end of the cylindrical section 31c constant when the substrate is rotated.

A lower surface of the flange section 33c is provided in a tapered shape projecting downward. The tapered shape engages with a downwardly indented tapered section of the recovery tool holder 24. A groove section engaging with an opening of the container 41 is formed at a lower side of the tapered shape.

The drive unit 20 is a unit for moving the recovery tool 30 in a horizontal direction, and comprises a horizontal arm 21, an arm rotation shaft 22, an arm rotation base 23, and a recovery tool holder 24.

The horizontal arm 21 has a bridged structure with the recovery tool holder 24 fixed at a front end, and the arm rotation shaft 22 at a rear end.

The arm rotation shaft 22 is a structure with a rear end of the horizontal arm fixed, rotating around a vertical rotational axis.

The arm rotation base 23 is a structure with the arm rotation shaft 22 held rotatably, attached to the lower structure 3. FIG. 1 shows that the side surface of the arm rotation base 23 has a circular peripheral surface.

The recovery tool holder 24 is a structure for holding the recovery tool. A front end of the recovery tool holder 24 has a downwardly concave tapered section for engaging from below with a downwardly convex tapered section below the recovery tool 30, with part being an annular structure having a cut away section.

If the recovery tool 30 is pulled sideways, it passes through the cut away section and is removed from the recovery tool holder 24.

The recovery tool setting unit 40 is a unit for transferring the recovery tool to the drive unit 20, and is provided on an upper surface of the lower structure 3. The recovery tool setting unit 40 straddles the container 41 from below the recovery tool 30, and can cover the cylindrical sections 31a, 31b, 31c of the recovery tool 30. By operating the recovery tool setting unit 40, an operator can cause the container 41 and the recovery tool 30 to go up and down.

When setting the recovery tool 30 in the substrate inspection device 2, the following procedure is used.

The operator handles the recovery tool 30 and the container 41 together. The operator sets the container 41 and the recovery tool 30 in the recovery tool setting unit 40.

The container 41 and the recovery tool 30 are picked up using the recovery tool setting unit 40. The drive unit 20 is moved to place the recovery tool holder 24 below the recovery tool 30. The container 41 and the recovery tool 30 are lowered using the recovery tool setting unit 40. The recovery tool 30 is engaged with the recovery tool holder 24. The drive unit 20 is then moved to carry out substrate inspection.

When removing the recovery tool 30 from the substrate inspection device 2, the above procedure is simply reversed.

Figure 5:
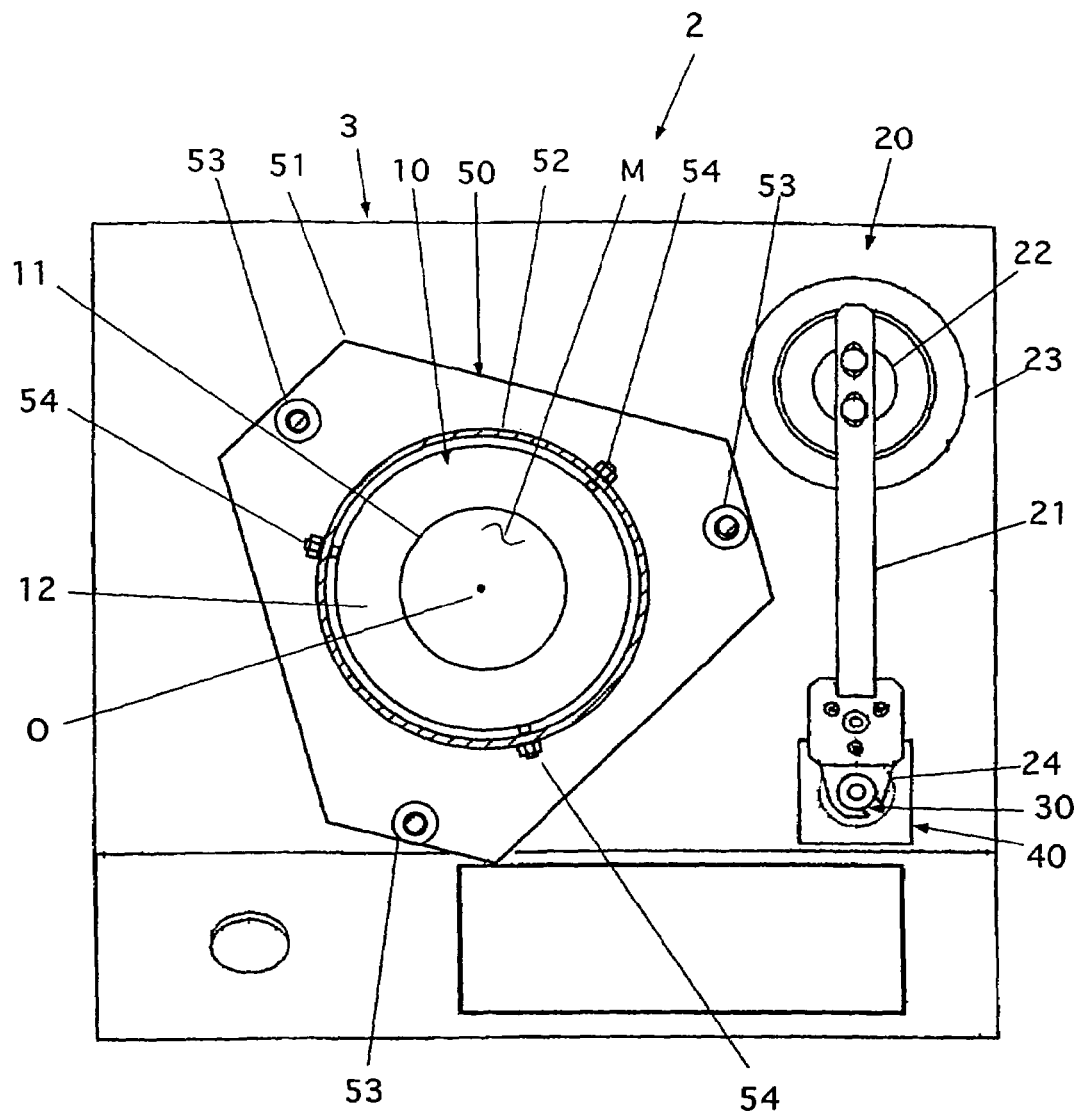
FIG. 5 is a III-III cross section of a substrate inspection device of an embodiment of the present invention.

FIG. 5 shows a relationship between the base 50 and the substrate rotating device 10.

The base 50 is a fundamental structure for carrying out positioning of the substrate, and comprises a base plate member 51, a base cylindrical member 52, base vertical guides 53, and base positioning mechanisms 54.

The base plate member 51 is a plate-member with a leveled upper surface, and is mounted on an upper section of the lower structure 3.

The base cylindrical member 52 is a cylindrical member having a vertical center axis, with a lower section connecting with the base plate member 51.

The base vertical guides 53 are column members having a vertical central axis, respectively fixed at three locations on the circumference of the upper side of the base plate member.

FIG. 5 shows that the base vertical guides 53 consist of three hollow columns, fixed at three locations on the circumference of the base plate member 51.

The base positioning mechanisms 54 are mechanisms that can align the center axis of the base cylindrical member with the rotational center axis. The base positioning mechanisms 54 preferably have a set screw for adjusting the size of a clearance between a side surface of the substrate holding base 12 and an inner surface of the base cylindrical member 52.

FIG. 5 shows that the base positioning mechanisms 54 have three set screws and nuts screwed into three locations on the circumference of the base cylindrical member 52. The nuts are screwed on to the set screws and lock the set screws.

Figure 4:
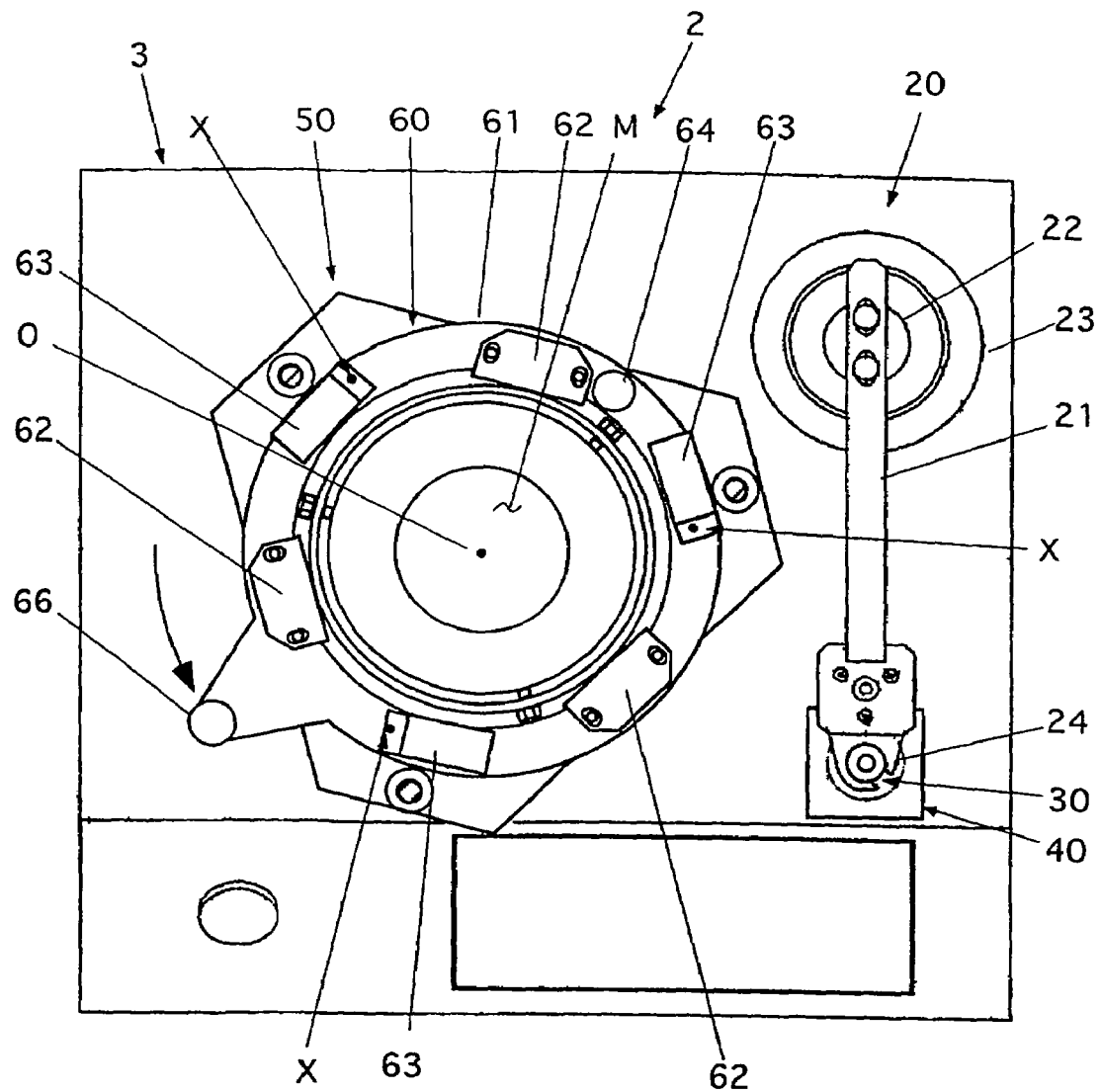
FIG. 4 is a II-II cross section of a substrate inspection device of an embodiment of the present invention.
Figure 6:
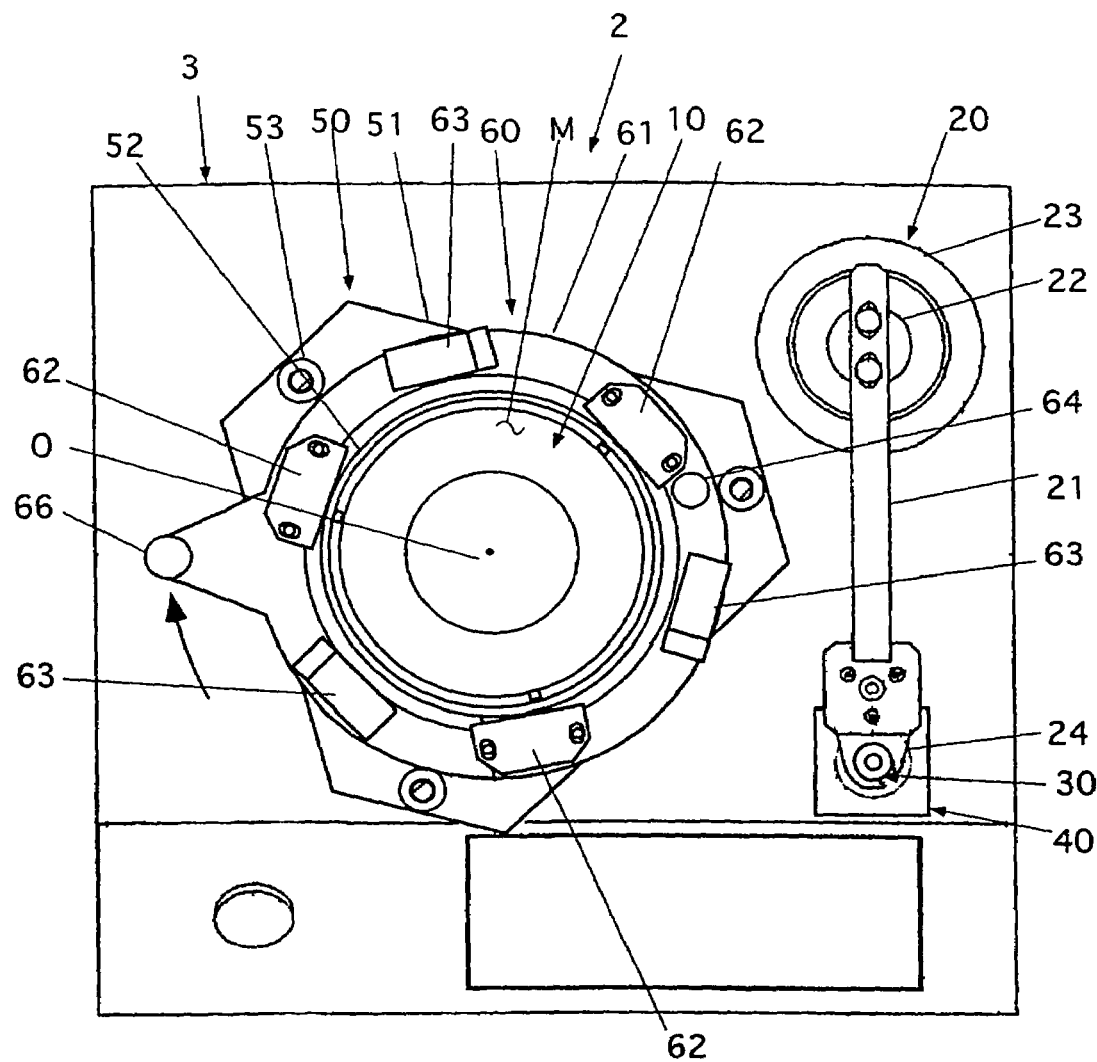
FIG. 6 is a III-III cross section of a substrate inspection device of an embodiment of the present invention.

FIGS. 4 and 6 show a relationship between the base 50, the disk 60, and the substrate rotating device 10.

The disk 60 is a mechanism for making the lifter 70, which will be described later, go up and down, and comprises a disk body and three lift cams 63.

The disk body is a structure rotatably supported in the horizontal direction with the rotational center axis as a center, and comprises a disk plate member 61, three peripheral guides 62, a single support 64, three slide supports 65, and a handle 66.

The disk plate member 61 is a plate-shaped member, and is movably supported in the horizontal direction on an upper surface of the base plate member at three locations on the circumference with a rotational center axis O of the lower side as a center.

FIGS. 4 and 6 show that the disk plate member 61 has an annular shape, and is a plate member spreading outward at one location.

The circumferential guides 62 are fixed to the disk plate member 61, and respectively contact three locations on the outer peripheral surface of the base cylindrical member 52 in a sliding manner.

The lift cams 63 are respectively fixed on the upper side of the disk body at three locations on the circumference. The upper surfaces of the lift cams 63 constitute cam faces. The cam faces comprise an inclined surface K that is inclined downwards in one rotational direction in the circumferential direction with the rotational center axis O as a center, and a horizontal surface L continuing on from the upper side of the inclined surface K without a gap.

The support 64 is a column member provided at one location on the disk plate member. The height of the support 64 is the same size as the height of the horizontal surfaces L of the lift cams 63.

The slide supports 65 are column members fixed at three places to the lower surface of the disk plate body 61. Lower surfaces of the slide supports 65 slide on the upper surface of the base plate member 51.

The handle 66 is a column member fixed to the disk plate body 61, with a side surface constituting a grip section.

If the operator operates the handle 66, the disk 60 slides on the upper surface of the base 50 with the rotational center axis O as a center.

The lifter 70 is a structure having a support surface N capable of having a substrate mounted on an upper side, and moves up and down with rotation of the disk 60, and is made up of a lifter body and three lifter driven sections 74.

The lifter body is a structure movably guided vertically on the base and having restricted rotation, and is comprised of a lifter plate member 71, three wafer holders 72, and three lifter vertical guides 73.

The lifter plate body 71 is a plate member having a support surface N capable of mounting a substrate 1 on an upper side. The lifter plate member 71 is provided with a plurality of holes aligned in the radial direction at specified intervals, at three locations on the circumference.

The wafer holders 72 are respectively arranged at three locations on the circumference of the support surface N of the lifter plate member 71 and are fixed in a detachable manner. The edge of a substrate that has been placed on the support surface is brought into contact with the three wafer holders 72 from the periphery, and the substrate 1 is positioned on the lifter 70. The wafer holders 72 engage in holes provided in the lifter plate member 71. By selecting the holes that the wafer holders 72 fit into, it is possible to handle wafers of various diameters.

The lifter vertical guides 73 are column members having a vertical central axis, respectively fixed at three locations on the lifter plate member 71. Either the base vertical guides 53 or the lifter vertical guides 73 have hollow sections, while the others fit into the hollow sections, with the lifter 70 being guided so as to be vertical on the base 50 with restricted rotation.

The lifter driven sections 74 are members respectively projecting to and fixed at three locations on the circumference of the lifter plate member 71. Lower sides of the three lifter driven sections are respectively brought into contact with three cam faces, in a sliding manner at respective contact points X.

Figures 7A, 7B, 7C:
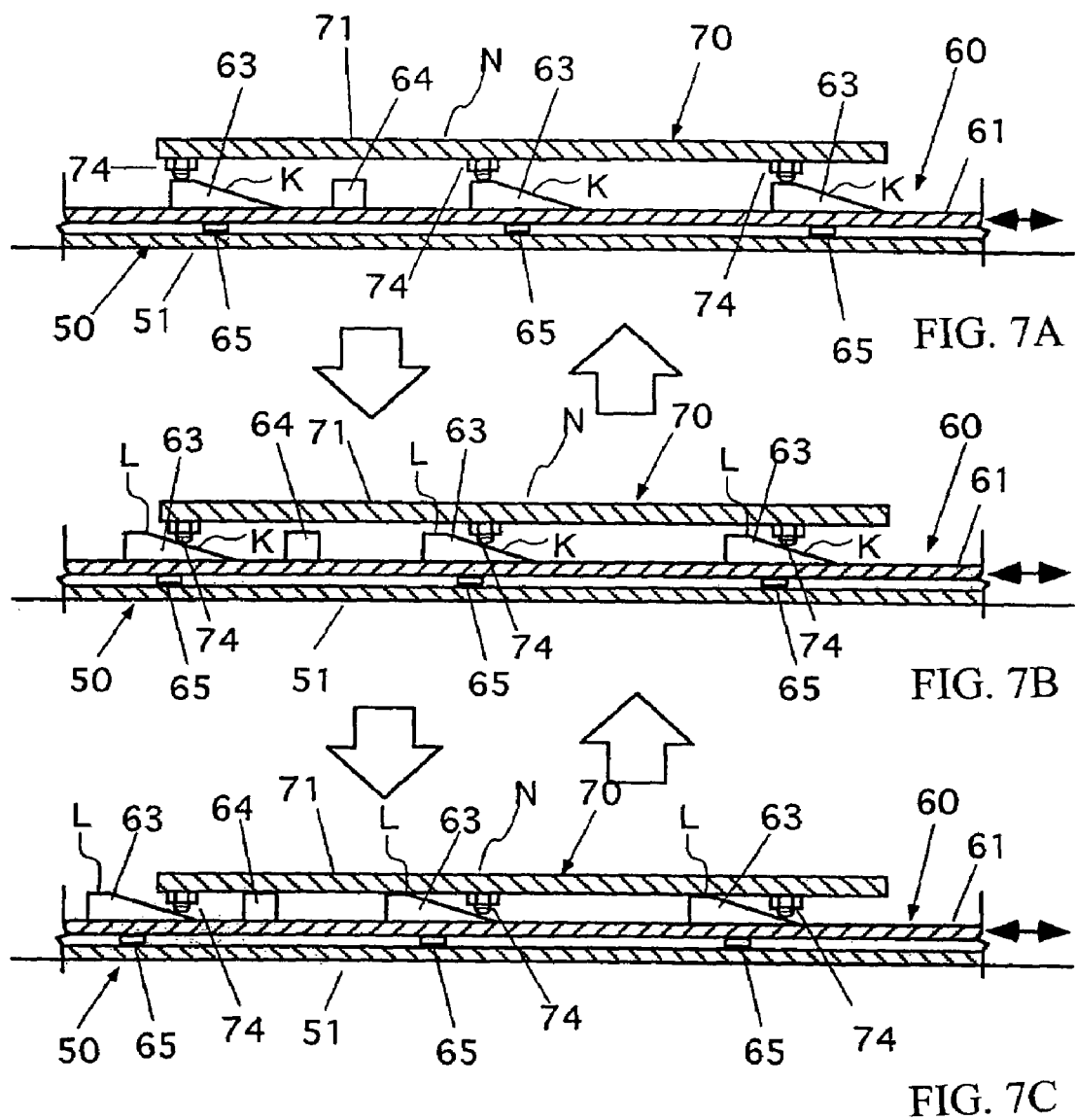
FIG. 7A-is a I-I cross section of a substrate inspection device of an embodiment of the present invention.
FIG. 7B is a I-I cross section of a substrate inspection device of an embodiment of the present invention.
FIG. 7C is a I-I cross section of a substrate inspection device of an embodiment of the present invention.

FIG. 7 shows that the lifter driven sections 74 are set screws screwed in to the lifter plate member 71 and locked with nuts, that lower ends have an annular shape, and that contact points X are points.

If the contact points X are moved to the upper side of the inclined surfaces K, the support surface N becomes higher than the holding surface M. If the contact points X are moved further to the upper side of the inclined surfaces K, the contact points X mount the horizontal surface L.

If the contact points X are moved to the lower side of the inclined surfaces K, the support surface N becomes lower than the holding surface M. If the contact points are moved further to the lower side of the inclined surfaces K, the lower surface of the lifter plate member 71 strikes the horizontal surface L, and the lower ends of the lifter driven section 74 are separated from the cam faces.

In the following, operation of a substrate inspection device of an embodiment of the present invention will be described, based on the drawings.

In the following, description will be given where the substrate is a semiconductor wafer, and a droplet is HF solution.

Initially, the case where a first type recovery tool 30a is used will be described.

Substrate Inspection Device Preparation Step

The substrate inspection device is prepared.

The recovery tool holder 24 is for handling a first type recovery tool 30a.

The container 41 and the recovery tool 30a are set together in the recovery tool setting unit 40. The recovery tool setting unit 40 is operated to engage the recovery tool 30a in the recovery tool holder 24.

FIG. 8A shows the structure of the first type recovery tool 30a fitted into the recovery tool holder 24.

The lifter 70 is positioned above. Lower ends of the lifter driven sections 74 are supported on the horizontal surface of the lift cams.

Substrate Setting Step

A substrate that has been bleached in advance in an atmosphere of vapor of HF solution is mounted on the support surface N of the lifter 70. Droplets of HF solution are adhered to the surface of the substrate 1.

Edges of the three wafer holders 72 are pressed, which positions the substrate 1.

The handle 66 is moved to rotate the disk 60. In FIG. 1, rotation is in a clockwise direction.

The disk 60 is guided on the base 50, and rotates about the rotational center axis. Lower ends of the lifter driven sections 74 move from the horizontal surface L to the inclined surface K along the cam faces of the lift cams 63.

Frictional force at contact points causes the lifter 70 to rotate about the rotational center axis, and play of the base vertical guides 53 and the lifter vertical guides 73 is offset to one side.

The substrate 1 is mounted on the holding surface M.

The lifter 70 is mounted on horizontal surfaces L of two lift cams 63 and the upper surface of the support 64.

Droplet Dripping Step

A droplet of HF solution is dripped into the internal space H of the recovery tool 30a.

A droplet 4 accumulates in the internal space H. Part of the droplet 4 is forced out to the groove 32a.

Substrate Scanning Step

The drive mechanism 20 holds the recovery tool 30a so that a droplet exposed to the groove 32a is brought into contact with the edge of the substrate 1.

FIG. 8B shows the recovery tool 30a driven by the drive unit 20.

The substrate rotating device 10 rotates the substrate 1 held on the holding surface about the rotational center axis.

The substrate 1 is rotated in a state where the droplet accumulated in the recovery tool 30a is adhered to the edge of the substrate 1.

Droplet Recovery Step

The drive mechanism 20 moves the recovery tool 30a above the recovery tool setting unit 40.

If the container 41 is moved upward, the upper end of the container 41 fits into a groove of the lower section of the recovery tool 30a.

The container 41 and the recovery tool 30a then rise upward as one.

The operator removes the recovery tool 30a and the container 41 from the substrate inspection device together.

FIG. 8C shows the container 41 and the recovery tool 30a in an integrated fashion.

(Impurity Measuring Step)

A droplet 4 moves into the container 41, and the amount of impurities contained in the droplet is measured.

Next, a case where a second type recovery tool 30b is used will be described.

Substrate Inspection Device Preparation Step

The substrate inspection device is prepared.

The recovery tool holder 24 is for handling a second type of recovery tool 30b.

The container 41 and the recovery tool 30b are set together in the recovery tool setting unit 40. The recovery tool setting unit 40 is operated to engage the recovery tool 30b in the recovery tool holder 24.

Figure 9A:
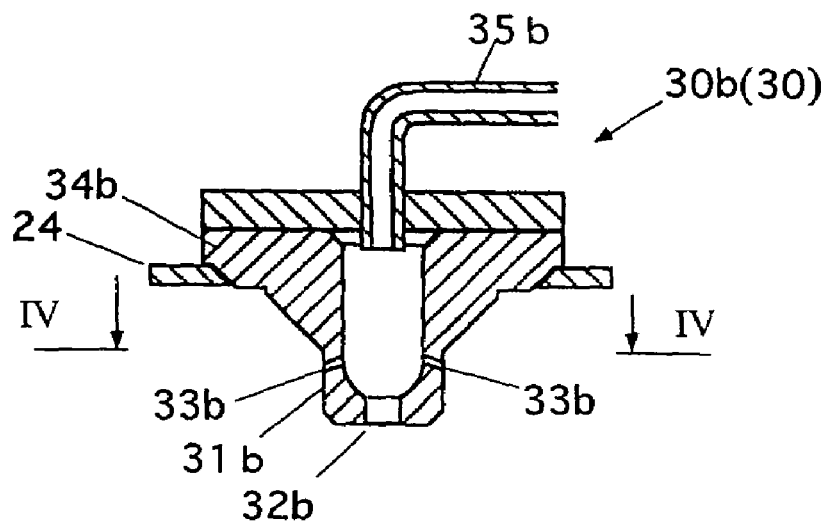
FIG. 9A is a cross section of a recovery tool of an embodiment of the present invention.

FIG. 9A shows the structure of the second type of recovery tool 30b fitted into the recovery tool holder 24.

The lifter 70 is positioned above. Lower ends of the lifter driven sections 74 are supported on the horizontal surface of the lift cams.

Substrate Setting Step

A substrate having an oxide film on the surface is mounted on the support surface N of the lifter 70.

The substrate is a silicon wafer, for example. An oxide film on the surface of the silicon wafer has hydrophilic properties with respect to HF solution.

Edges of the three wafer holders 72 are pressed, which positions the substrate 1.

The handle 66 is moved to rotate the disk 60. In FIG. 1, rotation is in a clockwise direction.

The disk 60 is guided on the base 50, and rotates about the rotational center axis. Lower ends of the lifter driven sections 74 move from the horizontal surface L to the inclined surface K along the cam faces of the lift cams 63.

Frictional force at contact points causes the lifter 70 to rotate about the rotational center axis, and play of the base vertical guides 53 and the lifter vertical guides 73 are offset to one side.

The substrate 1 is mounted on the holding surface M.

The lifter 70 is mounted on horizontal surfaces L of two lift cams 63 and the upper surface of the support 64.

Droplet Dripping Step

A droplet of HF solution is dripped into the internal space H of the recovery tool 30b.

The droplet 4 accumulates in the internal space H. Part of the droplet 4 is forced out to the first through hole 32b.

Negative Pressure Maintaining Step

The negative pressure means is operated, and a pressure of the internal space H is maintained at a more negative pressure than the atmospheric pressure.

Negative pressure draws a droplet accumulated in the internal space H upward.

Vapor passes from the outer side space of the side section through the second through holes 33b and enters into the internal space H, causing swirling.

Substrate Scanning Step

The drive unit 20 causes horizontal movement at a specified speed, while keeping a distance between the surface of the substrate 1 and the lower end of the cylindrical section constant.

Figure 9B:
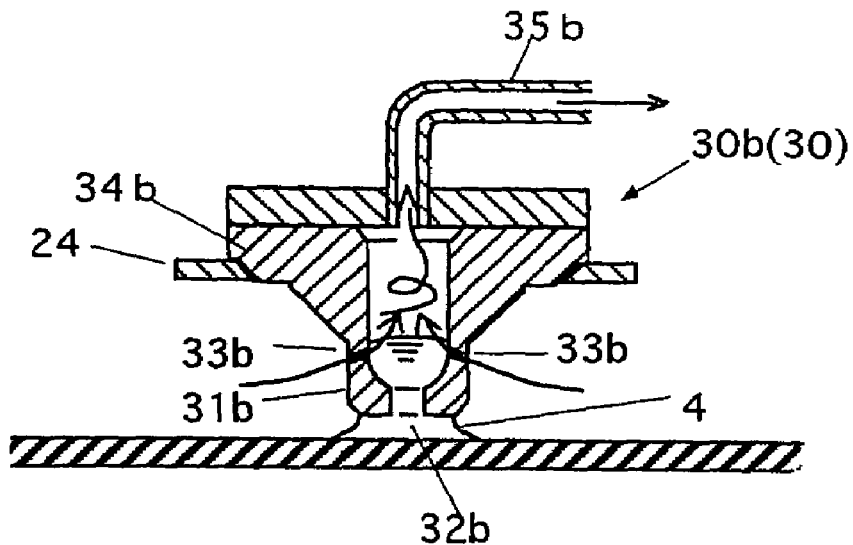
FIG. 9B is a cross section of a recovery tool of an embodiment of the present invention.

FIG. 9B shows the recovery tool 30b driven by the drive unit 20.

The substrate rotating device 10 rotates the substrate 1 held on the holding surface M about the rotational center axis.

The substrate 1 is rotated in a state where a droplet that has accumulated in the recovery tool 30b is adhered to the surface of the substrate 1.

A droplet of HF solution is moved while dissolving the oxide film on the surface of the substrate. Impurities contained in the oxide film are absorbed into the droplet. If the oxide film is removed from the surface of the substrate, the base material is exposed on the surface of the substrate.

If the rotational movement position of the substrate rotating device 10 and horizontal movement position of the drive unit 20 are linked, it is possible to dissolve only an oxide film on a specified region of the surface of the substrate.

Droplet Recovery Step

The drive mechanism 20 moves the recovery tool 30b above the recovery tool setting unit 40.

If the container 41 is moved upward, the upper end of the container 41 fits into a groove of the lower section of the recovery tool 30b.

The container 41 and the recovery tool 30b then rise upward as one.

The operator removes the recovery tool 30b and the container 41 from the substrate inspection device together.

Figure 9C:
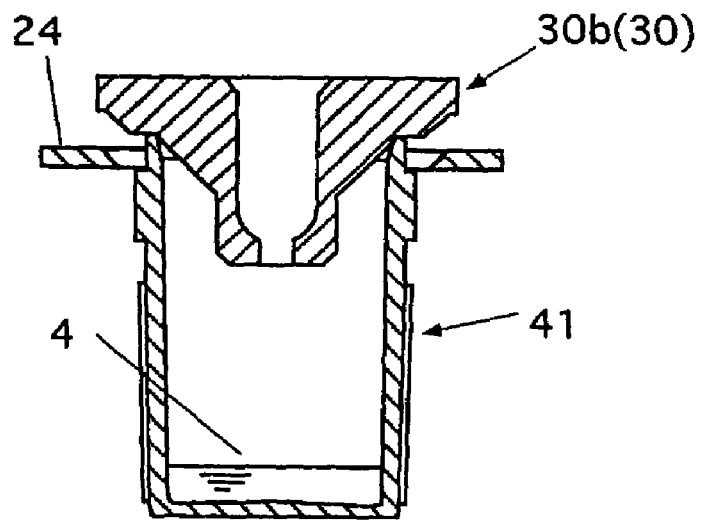
FIG. 9C is a cross section of a recovery tool of an embodiment of the present invention.
Figure 10:
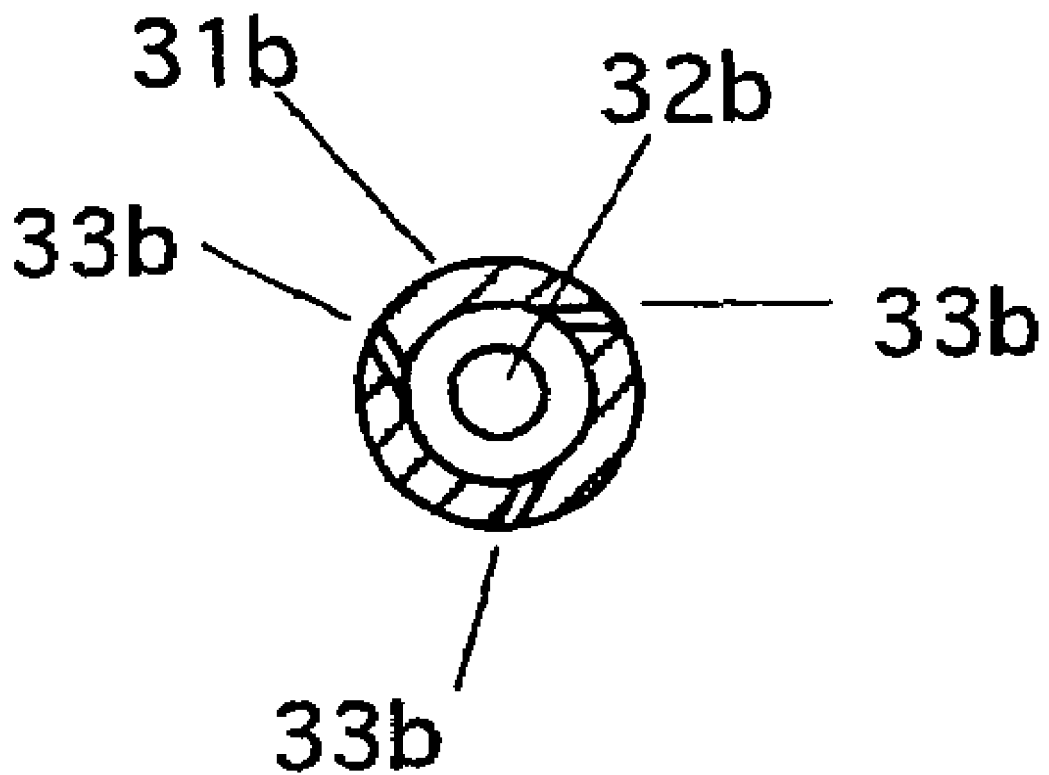
FIG. 10 is a IV-IV cross section of a recovery tool of an embodiment of the present invention.

FIG. 9C shows the container 41 and the recovery tool 30b in an integrated fashion.

Impurity Measuring Step

A droplet 4 moves into the container 41, and the amount of impurities contained in the droplet is measured.

Next, the case where a third type of recovery tool 30c is used will be described.

Substrate Inspection Device Preparation Step

The substrate inspection device is prepared.

The recovery tool holder 24 is for handling a third type recovery tool 30c.

The container 41 and the recovery tool 30c are set together in the recovery tool setting unit 40. The recovery tool setting unit 40 is operated to engage the recovery tool 30c in the recovery tool holder 24.

FIG. 11A shows the structure of the third type recovery tool 30c fitted into the recovery tool holder 24.

The lifter 70 is positioned above. Lower ends of the lifter driven sections 74 are supported on the horizontal surface of the lift cams.

Substrate Setting Step

A substrate that has been bleached in advance in an atmosphere of vapor of HF solution is mounted on the support surface N of the lifter 70. Droplets of HF solution are adhered to the surface of the substrate 1.

Edges of the three wafer holders 72 are pressed, which positions the substrate 1.

The handle 66 is moved to rotate the disk 60. In FIG. 1, rotation is in a clockwise direction.

The disk 60 is guided in the base 50, and rotates about the rotational center axis. Lower ends of the lifter driven sections 74 move from the horizontal surface L to the inclined surface K along the cam faces of the lift cams 63.

Frictional force at contact points causes the lifter 70 to rotate about the rotational center axis, and play of the base vertical guides 53 and the lifter vertical guides 73 are offset to one side.

The substrate 1 is mounted on the holding surface M.

The lifter 70 is mounted on horizontal surfaces L of two lift cams 63 and the upper surface of the support 64.

Droplet Dripping Step

A droplet of HF solution is dripped into the internal space H of the recovery tool 30c.

A droplet 4 accumulates in the internal space H. Part of the droplet 4 is forced out to the first through hole 32c.

Substrate Scanning Step

The drive unit 20 causes horizontal movement at a specified speed, while keeping a distance between the surface of the substrate 1 and the lower end of the cylindrical section constant.

FIG. 11B shows the recovery tool 30c driven by the drive unit 20.

The substrate rotating device 10 rotates the substrate 1 held on the holding surface M about the rotational center axis.

The substrate 1 is rotated in a state where a droplet accumulated in the recovery tool 30c is adhered to the surface of the substrate 1.

A droplet of HF solution is moved while adhering to the surface of the substrate. Liquid containing impurities is absorbed into the droplet, If the rotational movement position of the substrate rotating device 10 and horizontal movement position of the drive unit 20 are linked, it is possible to recover solution at a specified region of the surface of the substrate.

Droplet Recovery Step

The drive mechanism 20 moves the recovery tool 30c above the recovery tool setting unit 40.

If the container 41 is moved upward, the upper end of the container 41 fits into a groove of the lower section of the recovery tool 30c.

The container 41 and the recovery tool 30c then rise upward as one.

The operator removes the recovery tool 30c and the container 41 from the substrate inspection device together.

FIG. 11C shows the container 41 and the recovery tool 30c in an integrated fashion.

Impurity Measuring Step

A droplet 4 moves into the container 41, and the amount of impurities contained in the droplet is measured.

If a substrate inspection device in accordance with one or more embodiments of the above-described embodiments is used, the following effects may be achieved.

The recovery tool is comprised of a cylindrical section and a flange section, a lower surface of the flange section forms a downwardly convex tapered section, and the tapered section fits into a tapered section of the recovery tool holder of the drive unit, which means that the recovery tool can be connected to the drive unit with a simple structure.

Also, since a step engaging with the upper end of the container is provided on a lower side of the flange section of the recovery tool, it is possible to use the container and the recovery tool in an integrated manner.

Also, since grooves extending horizontally are provided in the cylindrical section of the first type of recovery tool, with the grooves connecting the internal space with the atmosphere, the drive mechanism causes part of the droplet that has accumulated in the internal space forced out from the grooves to come into contact with the edge of the substrate, which means that the droplet is adhered to the edge of the substrate and caused to move along the edge.

Providing negative pressure maintaining means capable of maintaining the internal space at a negative pressure in the second type recovery tool means that it is possible to support drawing up a droplet in the internal space by the negative pressure.

Since the circumference of the first through hole of the lower end of the cylindrical section is an annular flat surface, the droplet settles between the lower end section and the surface of the substrate due to adhesive force, and it is difficult for a droplet to leak to the outside.

Further, since the second through holes crossing the radial direction are provided in the cylindrical section, atmospheric gas passes through the second through holes due to the negative pressure and enters the internal space, and is swirled around and sucked in, thus drawing up the droplet in the internal space.

Also, because the lifter is restricted on rotation in the base and movably guided in the vertical direction, and supported on the inclined surfaces of the cam lifts arranged at three places in the circumferential direction of the disk, if the disk is rotated the lifter moves vertically, and so the substrate is mounted on a support surface of the lifter at an upper position, and if the lifter is lowered it is possible to transfer the substrate to the holding surface of the substrate rotating device, and because frictional force presses the lifter in one rotational direction with the rotational center axis as a center, the guidance play of the disk and the lifter is offset to one side and positioning accuracy of the substrate is improved.

Also, cam faces of the lift cams are formed by a horizontal surface and an inclined surface, and when the lifter has been moved upward the lifter mounts the horizontal surface, which means the lifter is stopped at the upper position in a stable manner.

Also, since cam faces of the lift cams are formed by a horizontal surface and an inclined surface, and when the lifter has been moved downward the lifter mounts the horizontal surface, it is possible to stably stop the lifter at the lower position.

Since the cylindrical member is provided on the base, and the circumferential guides contacting three places on the outer surface of the cylinder section are fixed to the disk, the disk is accurately and stably rotated about a central point of the cylindrical member.

It is also possible to position the base with higher accuracy and with a simple structure, because the cylindrical member is provided on the base and base positioning mechanisms comprising set screws gripping the cylindrical member are provided, and it is possible to adjust a clearance between the cylindrical member and the base of the substrate rotating device.

Also, by providing the three wafer holders on the support surface of the lifter and pressing the edge of the substrate with the three wafer holders, it is possible to position the substrate on the lifter.

Also, because lifter vertical guides of the lifter and base vertical guides of the base are engaged, and engaged while being guided vertically, the lifter is movably guided in the vertical direction on the base, and so if the lifter is moved up and down by rotation of the disk, the lifter is pushed in one rotational direction by frictional force of the contact points and play with respect to engagement sections with the lifter vertical guides and the base vertical guides is offset to one side, which means that parts for switching mounting of a substrate on the lifter in the substrate rotating unit improve accuracy when repeatedly positioning the substrate.

If inspection of a substrate is carried out using the second type recovery tool, inspection of a substrate having an oxide film can be accomplished easily, and it is possible to scan only a specified region of the surface of a substrate with a droplet still adhered.

The present invention is not limited to the above-described embodiments, and various modifications are possible within the scope of the appended claims without departing from the spirit of the invention.

The invention claimed is:

1. A recovery tool, for adhering a droplet to a substrate and causing movement in order to inspect the substrate, comprising:
   a cylindrical section with a central axis oriented vertically, having an internal space capable of accumulating a droplet,
   wherein the cylindrical section is provided at a side section with a groove extending horizontally to connect the internal space to atmospheric space,
   wherein a width of the groove is larger than a thickness of the substrate, and
   wherein the droplet is adhered to an edge of the substrate.

2. A recovery tool, for adhering a droplet to a substrate and causing movement in order to inspect the substrate, comprising:
   a cylindrical section with a central axis oriented vertically, having an internal space capable of accumulating the droplet, and
   negative pressure maintaining means capable of maintaining pressure of the internal space at a pressure more negative than atmospheric pressure when a droplet has been accumulated in the internal space, wherein
   the cylindrical section is provided with a first through hole connecting the internal space to atmospheric space at a lower end.

3. The recovery tool of claim 2, wherein:
   the circumference of an edge of the first through hole at the lower end of the cylindrical section forms an annular level surface.

4. The recovery tool of claim 2, wherein:
   the cylindrical section is respectively provided at side sections with a plurality of second through holes having central axes that cross in the same direction with respect to the radial direction, and
   the second through holes connect the internal space and the atmospheric space.

5. The recovery tool of claim 2, wherein:
   the negative pressure maintaining means has a negative pressure pipe connecting to the internal space.

* * * * *